United States Patent [19]

Malvern, deceased

[11] Patent Number: Plant 6,360

[45] Date of Patent: Oct. 25, 1988

[54] CHRYSANTHEMUM PLANT NAMED MALVERN'S YELLOW DIGNITY

[75] Inventor: Richard W. Malvern, deceased, late of Manchester, Mo., by Keith M. Malvern, administrator

[73] Assignee: Ball Pan Am Plant Company, Parrish, Fla.

[21] Appl. No.: 14,779

[22] Filed: Feb. 13, 1987

Related U.S. Application Data

[63] Continuation of Ser. No. 815,169, Dec. 31, 1985, abandoned.

[51] Int. Cl.[4] ..... A01H 5/00

[52] U.S. Cl. ..... Plt./78

[58] Field of Search ..... Plt./78

*Primary Examiner*—Robert E. Bagwill

*Attorney, Agent, or Firm*—Schwartz, Jeffery, Schwaab, Mack, Blumenthan & Evans

[57] ABSTRACT

A chrysanthemum plant named Malvern's Yellow Dignity having the combined features of standard form, yellow ray floret color, and a high degree of curvature of ray florets.

1 Drawing Sheet

The present invention comprises a new and distinct cultivar of *Dentrenthema morifolium,* Ramat., previously *Chrysanthemum morifolium,* Ramat., hereinafter referred to by the cultivar name Malvern's Yellow Dignity.

Malvern's Yellow Dignity was discovered as a spontaneous mutation of the cultivar Malvern's Dignity, disclosed in a pending application of applicant. The new cultivar is similar in most respects to its parent, except for the ray florets which are an intense yellow, as opposed to the generally white florets of Malvern's Dignity.

Malvern's Yellow Dignity was discovered by applicant in the greenhouses of Richard Malvern Florist, Inc., Manchester, Mo. in February of 1981 growing in a cultivated area among plants of the parent cultivar.

The first act of asexual reproduction of Malvern's Yellow Dignity was accomplished when vegetative cuttings were taken from the selection in May of 1981 in a controlled environment in Manchester, Mo. by a technician working under formulations established and supervised by applicant. Horticultural examination of selected units initiated in August of 1981 has demonstrated that the combination of characteristics as herein disclosed for Malvern's Yellow Dignity are firmly fixed and are retained through successive generations of asexual reproduction.

Malvern's Yellow Dignity has not been observed under all possible environmental conditions. The phenotype may vary significantly with variations in environment such as temperature, light intensity and day length. The following observations, measurements and comparisons describe plants grown in Manchester, Mo. and Parrish, Fla. under greenhouse conditions which approximate those generally used in commercial practice.

The following traits have been repeatedly observed and are determined to be basic characteristics of Malvern's Yellow Dignity which in combination distinguish this chrysanthemum as a new and distinct cultivar:

1. Standard flower form.
2. Intense yellow ray floret color.
3. The ray florets are highly incurved, particularly when compared with the ray florets of Hartmann's Yellow Dignity, also a yellow standard. Hartmann's Yellow Dignity, disclosed in U.S. Plant Pat. No. 4,477, also has less intense yellow ray floret color.

Of the many commercial cultivars known to the present inventor, the most similar in comparison to Malvern's Yellow Dignity is Hartmann's Yellow Dignity and the parent cultivar Malvern's Dignity. In comparison to Hartmann's Yellow Dignity, Malvern's Yellow Dignity has a more incurved flower form, a darker yellow flower color, a slightly smaller flower diameter, and 3–4 days earlier flower response rate and stem strength of Malvern's Yellow Dignity are similar to those same characteristics of Hartmann's Yellow Dignity. The new cultivar is similar in most respects to its parent, but is distinguished therefrom by its yellow ray floret color.

The accompanying photographic drawing shows typical inflorescence and foliage characteristics of Malvern's Dignity and Malvern's Yellow Dignity. In the black and white photograph, the parent Malvern's Dignity appears on the left, and Malvern's Yellow Dignity on the right, with the color accurately depicting the true ray floret color.

In the following description, color references are made to The Royal Horticultural Society Colour Chart (R.H.S.). The color values were determined between 10:00 a.m. and 12:00 noon on Mar. 25, 1985 under fluorescent lights at Bradenton, Fla.

Classification:

*Botanical.*—*Dentrenthema morifolium,* Ramat., cv Malvern's Yellow Dignity.

*Commercial.*—Standard cut.

INFLORESCENCE

A. Capitulum:

*Form.*—Incurved.

*Type.*—Formal.

*Diameter across face.*—12–15 cm.

B. Corolla of ray florets:

*Color (general tonality from a distance of three meters).*—Yellow.

*Color (upper surface).*—R.H.S. 8A.

*Color (under surface).*—R.H.S. 8A.

C. Corolla of disc florets:

*Color (mature and immature).*—Insignificant.

D. Reproductive organs:

*Androecium.*—Present in disc florets only; insignificant.

*Gynoecium.*—Present in ray florets only; insignificant.

PLANT

A. General appearance:

*Height.*—2–6 meters, depending on culture.

B. Foliage:

*Color (upper surface).*—R.H.S. 147A.

*Color (under surface).*—R.H.S. 147B.

*Shape.*—Deeply lobed and slightly serrated.

I claim:

1. A new and distinct cultivar of chrysanthemum plant named Malvern's Yellow Dignity, as described and illustrated, and particularly characterized by the combined features of standard form, yellow ray floret color, and high degree of curvature of ray florets.

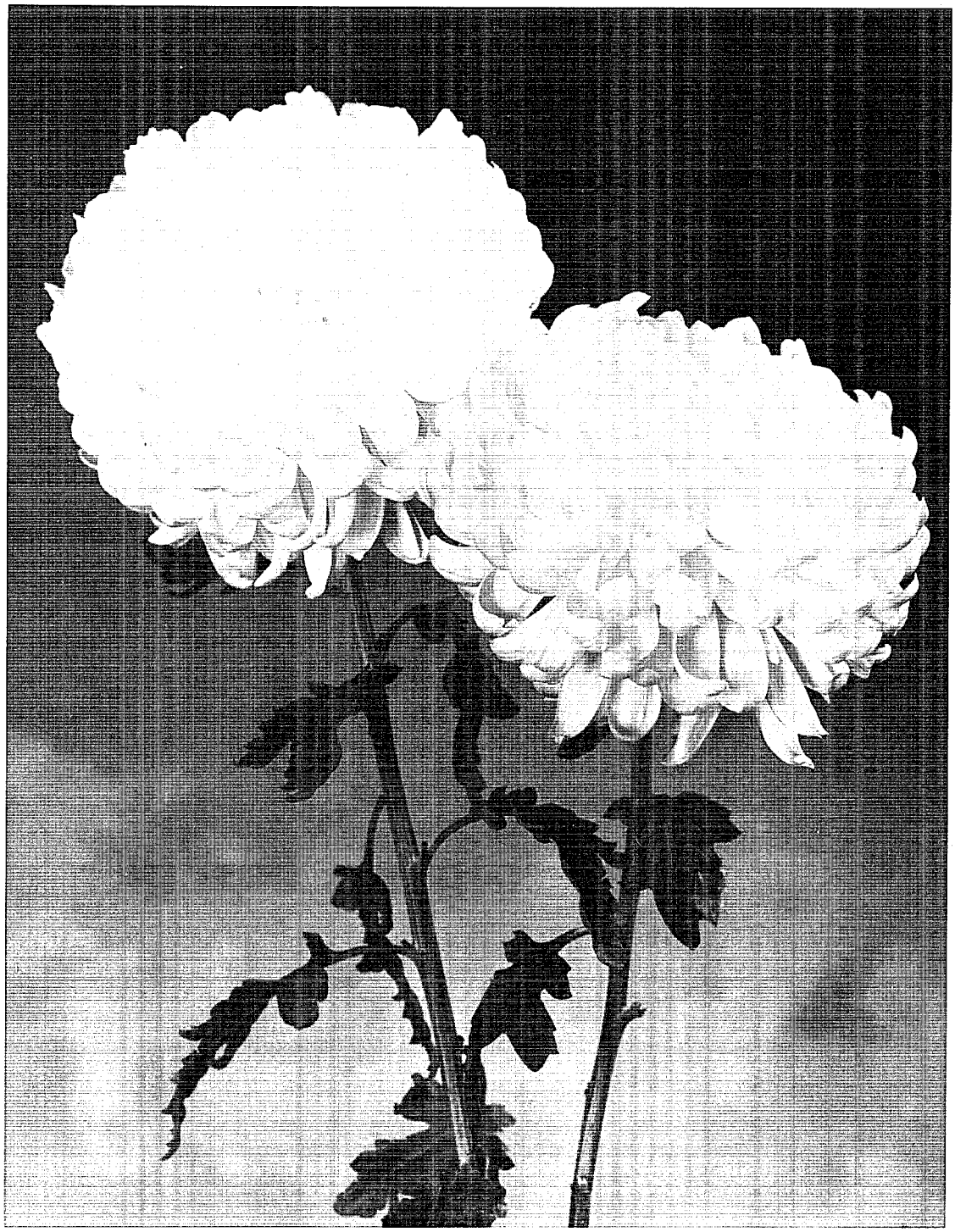

* * * * *